United States Patent [19]

Plaisted et al.

[11] Patent Number: 4,946,434
[45] Date of Patent: Aug. 7, 1990

[54] DISPOSABLE MANIFOLD AND VALVE

[75] Inventors: Richard Plaisted, Framingham; Richard M. Lueptow, Arlington, both of Mass.

[73] Assignee: Haemonetics Corporation, Braintree, Mass.

[21] Appl. No.: 152,078

[22] Filed: Feb. 4, 1988

Related U.S. Application Data

[63] Continuation-in-part of Ser. No. 90,325, Aug. 28, 1987, abandoned, which is a continuation-in-part of Ser. No. 888,764, Jul. 22, 1986, abandoned.

[51] Int. Cl.⁵ .......................... B04B 11/04; F16K 7/00
[52] U.S. Cl. ......................................... 494/29; 494/30; 137/625.46; 251/4
[58] Field of Search ....................... 494/37, 2, 5, 11, 27, 494/29, 30, 35, 22; 137/625.11, 625.12, 625.15, 625.13, 597, 624.11, 624.12, 624.13, 624.17, 624.18, 625.46; 251/4, 6, 9; 604/4–6, 30, 34, 250

[56] References Cited

U.S. PATENT DOCUMENTS

| | | | |
|---|---|---|---|
| DES. 250,085 | 10/1978 | Tuttle | D8/72 |
| 2,155,272 | 4/1939 | Jones | 137/624.18 |
| 2,298,967 | 10/1942 | Richardson | 137/624.18 |
| 2,345,073 | 3/1944 | Rosett | 137/624.13 |
| 2,367,319 | 1/1945 | Wahlberg | 137/624.13 |
| 2,517,452 | 8/1950 | Stindt | 137/624.13 |
| 2,579,598 | 12/1951 | Morrison | 137/624.18 |
| 2,678,159 | 5/1954 | Ellis . | |
| 2,838,270 | 6/1958 | Danielson | 251/110 |
| 3,016,915 | 1/1962 | Moeller, Jr. | 137/595 |
| 3,307,579 | 3/1967 | Beddoes | 137/624.13 |
| 3,411,534 | 11/1968 | Rose | 137/595 |
| 3,444,896 | 5/1969 | Van Der Veer | 137/624.2 |
| 3,459,182 | 8/1969 | Naftulin | 128/214 |
| 3,515,170 | 6/1970 | Mullaly | 137/636.1 |
| 3,536,451 | 10/1970 | Ludwin | 137/624.13 |
| 3,575,161 | 4/1971 | London | 128/2.05 |
| 3,587,644 | 6/1971 | Whitehouse | 137/624.13 |
| 3,749,285 | 7/1973 | Latham, Jr. | 222/58 |
| 3,805,842 | 4/1974 | Thompson et al. | 137/636.4 |
| 3,918,490 | 11/1975 | Goda | 137/597 |
| 3,920,215 | 11/1975 | Knauf | 251/7 |
| 3,960,224 | 6/1976 | Silvers | 177/47 |
| 3,985,134 | 10/1976 | Lissot et al. | 128/214 R |
| 4,061,142 | 12/1977 | Tuttle | 128/214 R |
| 4,360,007 | 11/1982 | Levy et al. | 128/I R |
| 4,457,339 | 7/1984 | Juan et al. | 137/624.16 |
| 4,464,167 | 8/1984 | Schoendorfer et al. | 604/6 |
| 4,482,342 | 11/1984 | Lueptow et al. | 494/21 |
| 4,668,214 | 5/1987 | Reeder | 494/37 |
| 4,821,996 | 4/1989 | Bellotti et al. | 251/4 |

FOREIGN PATENT DOCUMENTS 2700491 5/1978 Fed. Rep. of Germany .

*Primary Examiner*—Harvey C. Hornsby
*Assistant Examiner*—Joseph S. Machuga
*Attorney, Agent, or Firm*—Hamilton, Brook, Smith & Reynolds

[57] ABSTRACT

A disposable manifold and valve for fluid processing are claimed in which a manifold provides a plurality of sterile paths for directing the flow of fluids. A rotatable valve employs a cam to control the flow of fluids through the manifold. The valve and manifold system are suited for the processing of blood and particularly for the washing of shed blood retrieved during surgery.

20 Claims, 4 Drawing Sheets

DISPOSABLE MANIFOLD AND VALVE

RELATED APPLICATION

This application is a continuation-in-part of U.S. patent application Ser. No. 090,325, filed on Aug. 28, 1987, by Richard M. Lueptow and Thomas D. Headley entitled "Method and Apparatus for Cell Washing," which is a continuation-in-part of U.S. patent application Ser. No. 888,764, filed on July 22, 1986, by Thomas D. Headley both applications now abandoned.

BACKGROUND

The invention relates generally to valves for controlling the flow of fluids, and more particularly, relates to a disposable manifold for directing the flow of blood wherein a rotatable valve controls flow through the manifold.

A substantial volume of blood is shed during many major surgical procedures, such as heart by-pass surgery and hip replacement surgery. Often the shed blood, which has been contaminated, is discarded and replaced with donor blood. Recently, an alternative procedure has been developed in which the shed blood is recovered, the contaminants removed, and the "uncontaminated" blood cells reinfused into the patient.

In this procedure, the fluid in the surgical site is collected using suction and is drawn into an evacuated reservoir. The fluid collected in the reservoir, called "shed blood", contains whole blood, saline used to rinse the surgical site, blood clots, bone chips, fatty tissue and other miscellaneous contaminants.

The collected shed blood may be disposed of in at least three ways. First, it may be discarded and the lost blood volume replaced by donor blood.

A second alternative is to filter the shed blood and transfuse it to the patient. The filter removes blood clots, bone chips and tissue from the shed blood, but the filtered shed blood remains diluted with the saline originally used to rinse the surgical site.

The third alternative is to "wash" the shed blood, as well as filter it. One way of washing shed blood is to use a centrifugal wash system. (See "The Preparation of Leukocyte-Poor Red Blood Cells: A Comparative Study, Meryman et al., *Transfusion* 20(3): 285: 287, 1980.) In a typical centrifugal wash system, shed blood is centrifuged while washing it with saline in a disposable centrifuge bowl or rotor. A typical bowl for such a system is the so-called Latham bowl, shown in U.S. Pat. No. 4,300,717. Since red cells have a higher density than saline or blood plasma, the red cells fill the outermost portion of the rotating centrifuge bowl. As more shed blood enters the bowl, the red cells remain in the bowl displacing the supernatant (saline, plasma, contaminants, etc.) out of the bowl. This concentrates the red blood cells in the bowl. Next, saline is directed into the bowl, instead of shed blood. Saline, entering the bowl, is directed by the lower extended skirt portion of the core to the outermost radius of the bowl and through the bed of packed red blood cells. In this way, the supernatant is diluted and displaced by the saline until a satisfactory "washout" efficiency is obtained.

In the processing of shed blood, it is necessary to interconnect numerous devices and fluid reservoirs along sterile closed fluid pathways. Often this is done with flexible tubing wherein pneumatic, manual, or electrically actuated clamps or manual slide clamps are used to individually open or close various sections of tubing to control the fluid flow.

During the processing of the blood, the operator must manually open or close the clamps corresponding to the desired operation. This operator-dependent system can result in errors such as placing the tubing in the wrong clamps or operating the wrong clamp at an improper time. Additional time is required for operator training to insure efficient and safe use.

Many valve mechanisms that control fluid flow depend upon rotation of an inner member that defines a fluid pathway within an outer member. The relative position of the two members determines whether the fluid path is open or closed. A glass stopcock is one example of such a valve which utilizes a rotating seal such as an O-ring to prevent leakage. Such a seal is complex and in the present application presents problems of biocompatibility between the valve material and the blood.

Disclosure of the Invention

The present invention involves a single valve mechanism to simplify loading and operation of a sterile fluid control assembly. A disposable manifold is inserted into a valve assembly which is rotated through a four cycle process for washing blood described herein. The valve utilizes a cam comprised of a circular notched member that closes pathways through which the fluids can flow into or out of the manifold. By rotating the valve to each of the cycle positions, the appropriate fluids are directed through a junction within the manifold. The rotating member rotates about a spindle seated within a flange assembly. The flange assembly is comprised of a base and a hinged cover. The cover opens to permit loading of the manifold, and is locked in a closed position during processing.

The valve can be actuated both manually or automatically. A motor control system used to control a centrifuge used during the blood washing procedure can also be used to control valve operation. Alternatively, the manual operation of the valve can be used to control centrifuge operation.

The manifold and rotating valve are formed in such a way that the manifold can be inserted into the housing in only one configuration. This reduces the possibility of operator error arising from improper loading of tubing into the fluid control system. The manifold can be made by a simple mold using materials that are biocompatible with human blood. The pathway within the system is always closed, as the tubing can be solvent bonded to the manifold.

The only moving parts are the valve and the collapsable tubes that serve as ports to control the flow of fluid into and out of the manifold.

Referring now to the drawings, the invention will be described in greater detail.

DETAILED DESCRIPTION OF THE INVENTION

Figure 1:
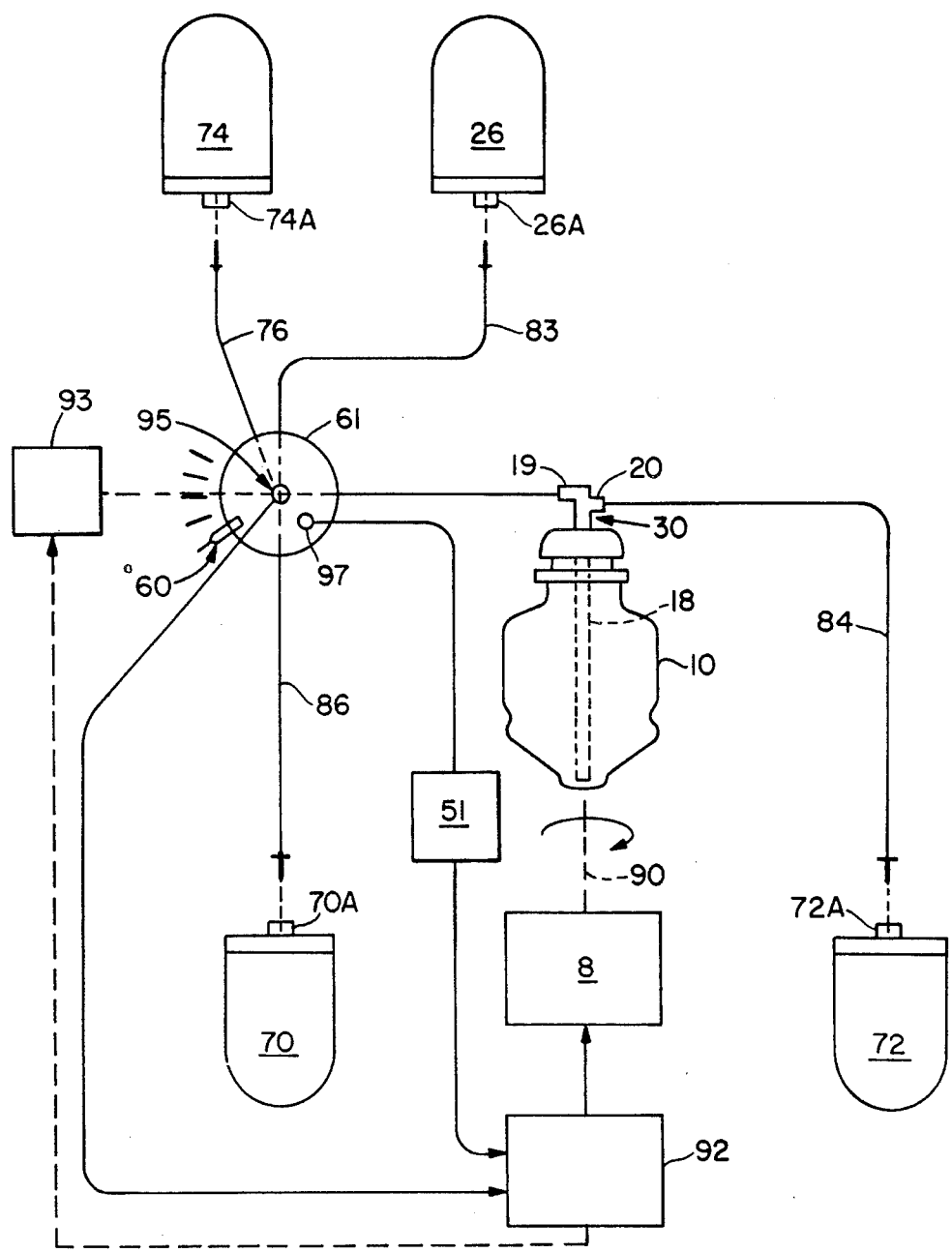
FIG. 1 schematically illustrates an apparatus used for the washing of blood.

A system for controlling the flow of fluids for the blood washing cycle of the present invention is schematically illustrated in FIG. 1. As shown in U.S. application Ser. No. 090,325, normally three clamps are used to control pathways 76, 83, 84, and 86 during each portion of the wash cycle. After loading of the disposable tubing assembly into each of the appropriate clamps which are then normally closed, the wash cycle can begin. The first portion of the cycle involves the opening of one clamp to permit a predetermined amount of blood to flow into a centrifuge bowl 10. In the second portion, the first clamp is closed and a second clamp is opened to permit a predetermined amount of wash solution to enter the centrifuge bowl 10. Both clamps are then closed and the fluid mixture is centrifuged in the third step of the cycle. The waste material is directed to a waste receptical 72 through line 84 and the washed blood is transmitted through a third open clamp along the tubing 86 to a reinfusion bag 70 during the final step of the cycle.

Figure 2:
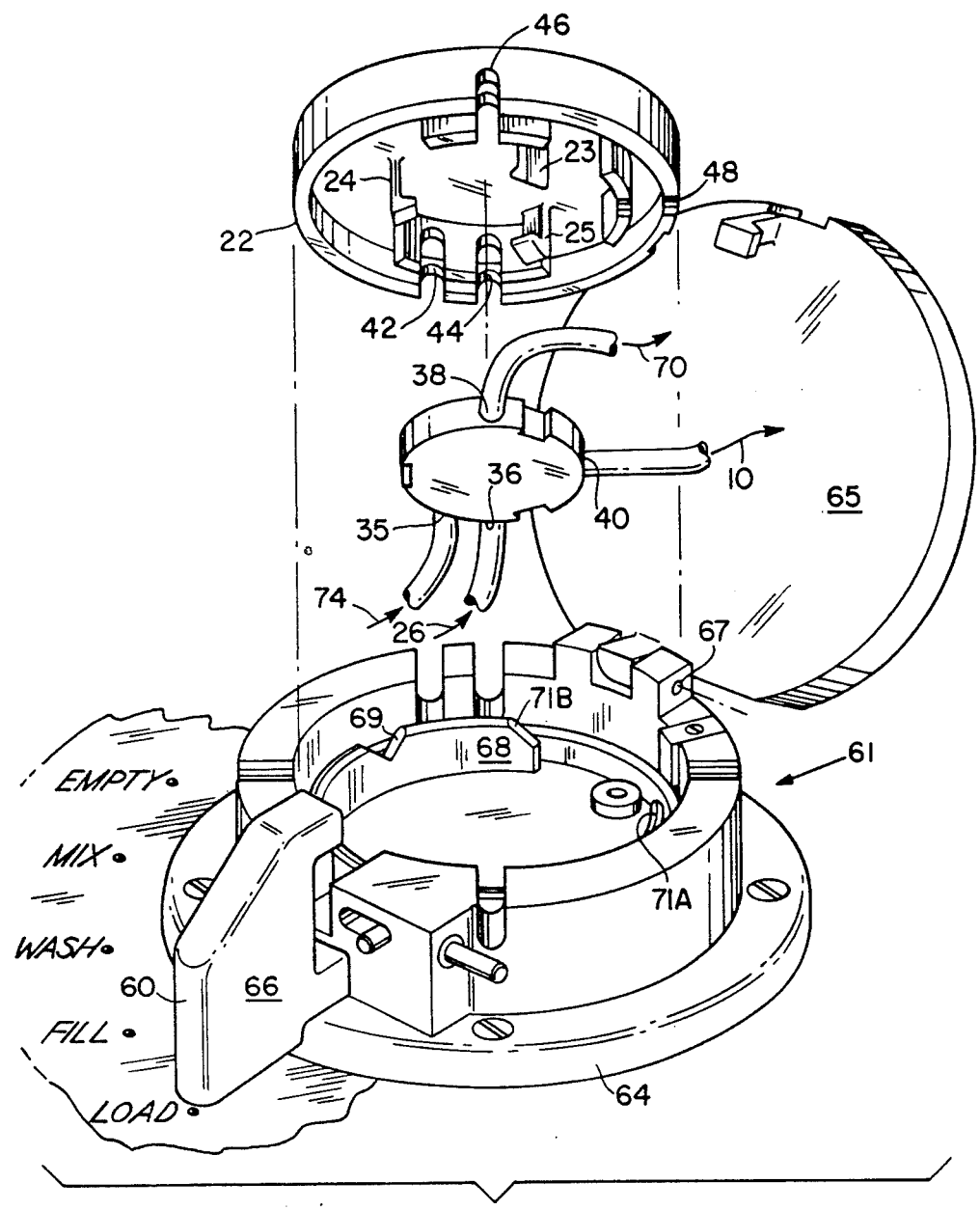
FIG. 2 is an exploded perspective view of the invention with the flange cover in the open position.

A preferred embodiment of the present invention replaces the three clamps, Y-junction and a section of tubing described in application U.S. Ser. No. 090,325, with the disposable manifold and valve system 61 shown in greater detail in FIG. 2.

The system is comprised of a disposable manifold 31 with tubes 76, 83, 84, and 86 extending into and sealed at openings on an outer surface of the manifold. The portions of the tubes 76, 83, 84, and 86 adjacent the manifold 31 form four ports 35, 36, 38, and 40, respectively, through which fluid flows from the blood reservoir 74 or the wash solution reservoir 26 and into the centrifuge bowl 10 or the product bag 70, respectively. The ports 35, 36, 38, and 40 can be portions of tubing which collapse to close the tube when pressure is applied to an outer surface of the tube.

Figures 3, 4:
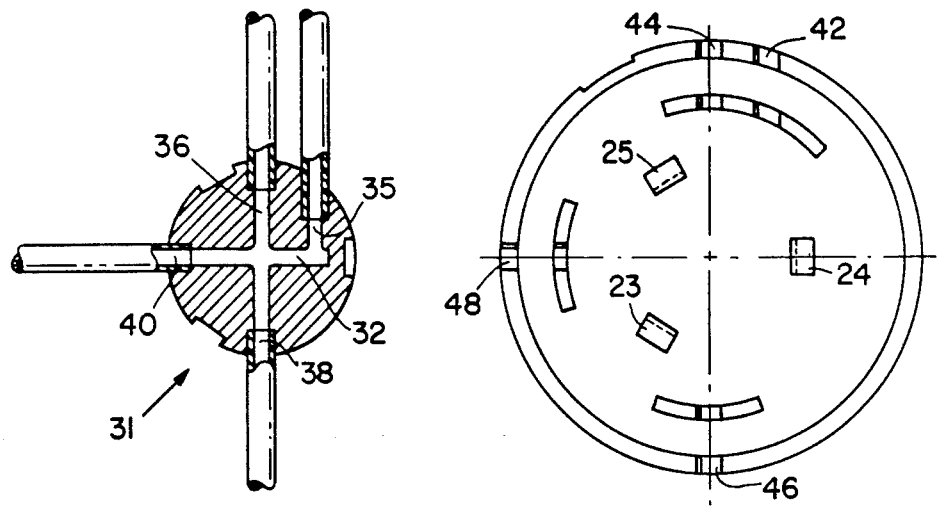
FIG. 3 is a cross-sectional plan view of the disposable manifold of the present invention.
FIG. 4 is a plan view of the inner housing in which the manifold is seated.

The manifold 31 is inserted into a molded guide 22, and is retained therein, preferably by a number of snap-in prongs 23, 24 and 25. The tubes 76, 83, 84, and 86 are centrifuged within port guides 42, 44, 46 and 48. As shown in FIG. 4, these port guides are formed by slots 42A, 44A, 46A and 48A in the outer wall 14 of the guide 22, and by slots 42B, 44B, 46B, and 48B formed in three inner wall portions 15, 16, and 17 of the guide 22. As will be seen, a cam 68 is positioned such that when the guide 22 is placed into the flange assembly 61, the cam moves in a circular motion between the outer wall 14 and the three inner wall portions 15, 16, and 17. Those portions of the tubes, 76, 83, 84, and 86 which come in contact with the cam 68 are the ports 35, 36, 38 and 40.

The valve 60 is comprised of a handle 66 and a cam 68. The partially circular cam 68 has a notch 69 and two beveled ends 71A and 71B. By grasping the handle 66 and rotating the attached cam 68 with respect to the flange assembly, the notch 69 and one of the beveled ends operate to open and close pathways leading into or out of the manifold 31 by compressing the tubing extending through port guides 42, 44, 46, and 48.

A preferred embodiment of the blood washing procedure for which this valve is particularly suited, utilizes the following processing sequence.

The operator first inserts the manifold 31 and guide 22, which have been molded and preassembled, into position within the rotating valve 60. The flange assembly cover 65 is then locked into the closed position with latch 50 after the handle 66 has been moved into the "Load" position. The following table indicates whether each port into or out of the manifold 31 is closed or open during each of the processing steps.

| Operation | Contaminated Product Port 35 | Wash Solution Port 36 | Wash Product Port 38 | Bowl Port 40 |
|---|---|---|---|---|
| Load | Closed | Closed | Closed | open |
| Fill | Open | Closed | Closed | open |
| Wash | Closed | Open | Closed | open |
| Mix | Closed | Closed | Closed | open |
| Empty | Closed | Closed | Open | open |

Referring again to FIGS. 1 and 2 a preferred embodiment of the wash system of the invention will now be described, in detail.

As shown in FIG. 1, fluid to be washed, such as shed blood or thawed glycerolized frozen red cells is stored in a blood reservoir 74. For simplicity, the following description will refer to shed blood; but it should be kept in mind that other contaminated body fluids may be washed to remove contaminants, in a similar fashion. Reservoir 74 and bags 26, 72 and 70 may comprise flexible blood compatible plastic bags or rigid containers. An outlet port 74A on blood reservoir 74 is connected to blood compatible tubing 76, which forms a pathway with port 35 into the manifold 31.

Blood reservoir 74 is suspended above the centrifuge bowl 10 so that whole blood may be fed by gravity through tubing 76, manifold 31 and tubing 82 to inlet port 19 of centrifuge bowl 10. Likewise, wash solution bag 26 is suspended above the centrifuge bowl 10 for gravity feed coupling to inlet port 19. Blood compatible tubing 83 is coupled to outlet port 26A at one end and forms a pathway through port 36 leading into the manifold 31. Tubing 83 is connected through the manifold 31 with tubing 82 and, ultimately, to inlet port 19 of centrifuge bowl 10.

Outlet or effluent port 20 of centrifuge bowl 10 is coupled via blood compatible tubing 84 to inlet port 72A of waste disposal bag 72 located below bags 26 and 74. Product collection bag 70 is also located below bowl 10 and connected via blood compatible tubing 86 forming a pathway through port 38 extending from manifold 31. Product collection bag 70 is disposed below centrifuge bowl 10, so that collected product may be siphoned out the inlet port 19 of the centrifuge bowl 10, as will be described later.

Centrifuge bowl 10 is mounted on a chuck (not shown) for mechanical rotation about its longitudinal axis (See FIG. 1) by motor 8 connected to bowl 10 by axle 90. Motor 8 is controlled in rotational speed by motor control 92.

In operation, bodily fluid for washing, such as shed blood, or thawed glycerolized frozen whole blood, is stored in reservoir 74. A wash solution, such as saline, in the case of shed blood or deglycerolizing solution, in the case of glycerized whole blood, is stored in wash solution bag 26. The valve is initially in the "Load" position, in which ports 35, 36, and 38 are closed.

Step 1: Fill: Introduce Shed Blood

In a preferred embodiment, the motor 8, for the centrifuge bowl 10, is energized by motor control 92, as a result of the manual rotation of handle 66 into the "Fill" position. There is a magnetic sensor 95 adjacent the valve which can indicate the position of the handle. Logic circuit 51 conveys this information to the motor control 92. Note that in another preferred embodiment, the operation of the valve and bowl can be entirely automated where the valve is sequenced through the process by motor control 92 as shown in dotted lines in FIG. 1 wherein motor control 92 provides a signal to activator 93 which mechanically activates manifold-/valve 61 to rotate the valve through various positions without human intervention.

The bowl 10 is rotated until it reaches a preferred angular rotational speed, on the order of 5800 revolutions per minute. The rotating centrifuge bowl is partially filled with blood from the blood reservoir 74 by the opening of port 35. Ports 36 and 38 are closed. Gravity feed from the blood reservoir 74 allows the shed blood to enter inlet port 19 and pass through the stationary header 30 and, ultimately, through the feed tube stem 18 to the lower portion of bowl 10. Under the influence of the centrifugal forces, red blood cells are concentrated, or packed, into an outer toroidal zone (not shown), while supernatant is left in an intermediate toroidal radially inwardly from the packed red blood cells.

Sterile air, previously contained within the centrifuge bowl, is located in the radially central coaxial region of the bowl body 10. The supernatant/red blood cell interface, and the supernatant/air interface may be visibly seen by an operator looking down onto the top of the centrifuge bowl. The supernatant is displaced out of the centrifuge bowl as more blood enters the bowl and the supernatant/red blood cell interface moves radially inward. The displaced supernatant exits the bowl via outlet port 20 and flows into waste disposal bag 72.

Step 2: Wash: Introduce Wash Solution

The centrifuge bowl 10 continues to fill with blood until the supernatant/red blood cell interface is slightly radially outward of a core within the bowl. After any excess supernatant has been expressed out port 20, the valve handle 66 is rotated to the "Wash" position, where port 35 is closed and port 36 is opened. Ports 38 remains closed. This allows wash solution from bag 26 to enter the bowl through inlet port 19, to dilute and displace the remaining supernatant out of the bowl via outlet port 20, to inlet port 72A of waste bag 72. This leaves a radially central air zone, toroidal layer of supernatant diluted with wash solution, and the toroidal layer of packed red blood cells. Note that, unlike the above-referenced prior art Latham cell washing bowl, the introduced wash solution is not forced by core skirts to enter at the lower interior bowl periphery and initially pass through the toroidal layer of packed red blood cells. Consequently, in the next step, a method for mixing the wash fluid and red blood cells is provided.

Step 3: Mix: Slow Down/Speed Up Motor

Next, port 35 is closed. The angular velocity of the bowl is abruptly slowed, utilizing motor control 92 to bring the rotational speed down to about 3600 RPM's. A magnetic sensor 97 can be used to indicate to the control 92 via logic circuit 51 that the valve is in the "mix" position. This causes the two layers, within the bowl to intermingle and the diluted supernatant to mix with the packed red blood cells. Turbulence control slots enhance the mixing of the wash solution and the supernatant by permitting turbulence to propagate into the supernatant. A substantial portion of any supernatant entrapped in the red cells is thereby mixed with the previously diluted supernatant. Next, the speed of the bowl is increased back to its normal rotational speed of 5800 RPM, causing the red cells to reconcentrate against the inner surface of the radial periphery of the bowl 10, leaving the diluted supernatant in the intermediate zone radially inwardly from the packed red blood cell layer.

Steps 2 and 3, above, may be repeated as necessary, until a satisfactory washout of supernatant is obtained by removing a sufficient amount of the initial supernatant from the red blood cells.

Step 4: Empty: Siphon Washed Red Cells Out of Bowl

When a satisfactory washout has been achieved, the motor 8 is braked by motor control 92 and the washed red blood cells become suspended in the wash solution. Ports 35 and 36 remain closed, while 38 is opened, to permit the suspended washed red blood cells to be siphoned from the bowl 10. The siphon is primed by pressing the side walls of waste bag 72, which causes the fluid in bowl 10 to siphon out the port 19 to tubes 82 and 86 through open port 38 to inlet port 70A into product bag 70.

The disposable portion of the valve consists of two interconnecting circular elements illustrated in detail in FIGS. 3 and 4. The first element is the manifold 31 with a fluid junction 32 at its center. The four ports 34, 36, 38, and 40 permit fluid flow into and out of the junction 32. The tubing 76, 83, 86, and 84 from the blood source, the washing solution source, and leading to the centrifuge and the reinfusion bag respectively are secured to the manifold 31.

Figure 5:
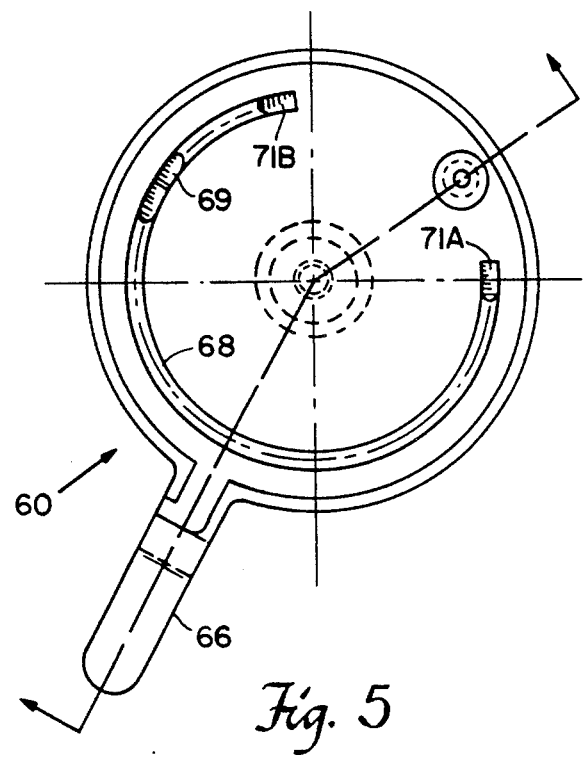
FIG. 5 is a plan view of the rotating valve.
Figure 6:
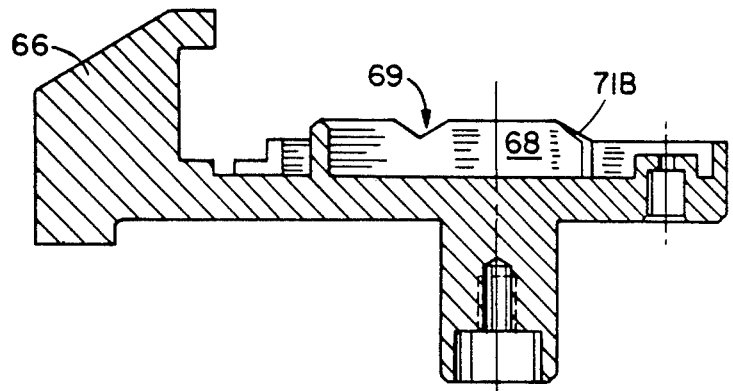
FIG. 6 is a cross sectional view of the valve of FIG. 5.

The rotating valve 60 is shown in greater detail in FIGS. 5 and 6. Note that the valve need not rotate, it can also be a sliding valve, or some other actuated device for opening and closing the pathways leading into and out of the junction 32. The valve 60 rotates about a spindle 62 situated at the center of a flange base 64.

The valve 60 is spring loaded at the base of the spindle 62 so that the closure of the cover forces the manifold 31 and guide 22 against the cam 68 which results in compression of the spring 65. The spring mount increases the dimensional tolerance of the system components.

The valve 60 has a handle 66 that is actuated by the operator to control the flow of fluid through the junction 32. The handle 66 has a lip 59 which extends over the top surface of the cover 65 except when the handle is in the "Load" position. In the "Load" position, a groove 56 in the cover 65 permits the cover to be opened. Thus, the lip 59 prevents the cover from being opened when the handle is in any of the "Fill," "Wash," "Mix," or "Empty" positions. The valve 60 is further comprised of a cam 68 having first and second beveled ends 71A and 71B, and a notch 69 disposed along a top portion thereof. The notch is configured to close ports 35 and 36 when the valve 60 is rotated to certain positions as required by the processing sequences being used. The cam elements are shaped so as to pinch the flexible tubing positioned within the ports 35, 36, and 38. The pinching of one of these tubes closes that pathway into the fluid junction.

The flange assembly 61 is comprised of base 64 and a cover 65. The cover 65 is hingeably attached to the base 64 at hinge 67. The cover 65 rotates to open and close the flange assembly 61 to permit the operator to easily insert and remove the disposable components 31 and 22. The cover 65 can be latched in the closed position as the pressure exerted by the cam on the tubing is opposed by a surface on the cover 65 that contacts one side of the tubing opposite the cam.

Equivalents

Those skilled in the art will recognize that there are many equivalents to the specific embodiments described herein. For example, instead of manually operable valves for opening and closing the fluid lines, solenoid valves or hydraulic valves may be employed, other type centrifuge bowls may be used, and pumps, instead of gravity fee, employed. Sophisticated monitoring and control techniques may also be employed to activate and monitor the process.

We claim:

1. A valve for controlling biological fluid flow comprising:
   (a) a manifold having a fluid junction and a plurality of fluid pathways in the manifold through which fluid can flow into and out of the junction; and
   (b) one flexible tube coupled to a respective one of the pathways;
   (c) a retainer having a bearing surface, the manifold being secured in a predetermined position in the retainer and the tubes also being secured in a predetermined position against said bearing surface on said retainer, and
   (d) a rotatable cam having a spindle loaded by a spring, said cam not in fluid communication with the pathways such that rotation of the cam relative to the manifold closes and opens selected tubes contacting the cam and bearing surface to control the flow of fluid through the junction;
   (e) a support member; and
   (f) a cover on said support member which, when the manifold retainer and tubes are loaded into the support member and said cover is closed, forces the manifold and retainer against the cam, resulting in compression of the spring.

2. The valve of claim 1 in combination with a centrifuge and a container wherein said plurality of tubes comprises:
   a first tube through which a first fluid flows into the junction;
   a second tube through which a second fluid flows into the junction;
   a third tube for directing the fluids from the junction into said centrifuge;
   a fourth tube through which a centrifuged fluid flows into a container.

3. The valve of claim 2 wherein said cam means includes a handle with a lip which extends over said cover when the cover is closed and said handle is disposed in any position, such that other than a loading position, said cover cannot be opened except in the loaded position.

4. The valve of claim 3 wherein the cam is rotatable between five selectable positions.

5. The valve of claim 4 wherein the first position is such that the first and second tubes are closed.

6. The valve of claim 4 wherein the second position is such that the first tube is open, the second tube is closed, and the fourth tube is closed.

7. The valve of claim 4 wherein the third position is such that the first tube is closed, the second tube is open, and the fourth tube is closed.

8. The valve of claim 4 wherein the fourth position is such that the first and second tubes are closed.

9. The valve of claim 4 wherein the fifth position is such that the first and second tubes are closed and the fourth tube is open.

10. The valve of claim 2 wherein said cam is comprised of a first element for closing the first and second tubes, and a second element for closing the fourth tube.

11. The valve of claim 2 wherein the first fluid is comprised of blood.

12. The valve of claim 11 wherein the second fluid is comprised of a solution for washing blood.

13. The valve of claim 1 wherein said manifold and retainer are disposable.

14. A valve for controlling the flow of fluids in a system for the washing of a biological fluid comprising:
    (a) a disposable manifold having a plurality of tubes sealed to the manifold which form fluid pathways for the flow of fluids into and out of the manifold; and
    (b) a guide means, with a bearing surface, said guide means retaining said manifold and tubes in a predetermined position in which the tubes are disposed against said bearing surface;
    (c) a support member to which said guide means with said manifold and tubes is attached in a predetermined position;
    (d) a cam, having a spindle loaded by a spring which cam is rotatable on said support member, said cam not being in fluid communication with said fluid, the manifold and guide means being mounted in said support member adjacent to said cam such that movement of the cam closes and opens selected tubes by compressing said tubes against said bearing surface to control the flow of fluid into and out of the manifold; and
    (e) a cover rotatably mounted on said support member and wherein when said cover is closed, it forces the manifold and guide means against the cam, resulting in compression of the spring.

15. The valve of claim 14 wherein said valve is manually actuated.

16. The valve of claim 14 wherein said valve is mechanically actuated.

17. The valve of claim 14 further comprising a sensor for detecting that the manifold is loaded onto the cam.

18. The valve of claim 14 wherein said cam is movable through a plurality of selectable positions such that each position is correlated with a closed or open position for each pathway.

19. The valve of claim 18 further comprising a sensor for detecting the position of the cam.

20. The valve of claim 18 wherein the guide means is loaded into the support means in a predetermined one of the selectable positions.

* * * * *

UNITED STATES PATENT AND TRADEMARK OFFICE
CERTIFICATE OF CORRECTION

PATENT NO. : 4,946,434

DATED : August 7, 1990

INVENTOR(S) : Richard Plaisted and Richard M. Lueptow

It is certified that error appears in the above-identified patent and that said Letters Patent is hereby corrected as shown below:

Column 7, line 41, after "manifold", insert ---,---.

Column 7, line 60, after ",", delete ---such that---.

Column 6, line 61, delete "loaded" and insert ---loading---.

Column 8, line 62, delete "means" and insert ---member---.

Signed and Sealed this

Thirty-first Day of December, 1991

Attest:

HARRY F. MANBECK, JR.

*Attesting Officer*   *Commissioner of Patents and Trademarks*